United States Patent [19]

McAlpine et al.

[11] 4,218,442
[45] Aug. 19, 1980

[54] 1-EPI-FORTIMICIN A AND DERIVATIVES

[75] Inventors: James B. McAlpine, Libertyville; Ronald E. Carney, Gurnee, both of Ill.

[73] Assignee: Abbott Laboratories, North Chicago, Ill.

[21] Appl. No.: 25,211

[22] Filed: Mar. 29, 1979

[51] Int. Cl.² ............................ A61K 31/71; C07H 15/22
[52] U.S. Cl. ..................................... 424/180; 536/17 R; 536/18
[58] Field of Search ......................... 536/17; 424/180

[56] References Cited

U.S. PATENT DOCUMENTS

| 4,078,138 | 3/1978 | Akita et al. | 536/17 |
| 4,091,032 | 5/1978 | Tadanier et al. | 536/17 |
| 4,124,756 | 11/1978 | Martin et al. | 536/17 |

*Primary Examiner*—Johnnie R. Brown
*Attorney, Agent, or Firm*—Robert L. Niblack; Gildo E. Fato; Joyce R. Niblack

[57] ABSTRACT

A 1-Epi fortimicin represented by the formula

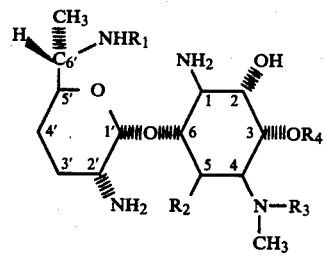

wherein: $R_1$ is hydrogen or loweralkyl; $R_2$ is hydrogen or hydroxyl, $R_3$ is selected from the group consisting of hydrogen, loweralkyl, aminoloweralkyl, diaminoloweralkyl, N-loweralkylaminoloweralkyl, N,N-diloweralkylaminoloweralkyl, hydroxyloweralkyl, aminohydroxyloweralkyl, N-loweralkylaminohydroxyloweralkyl, N,N-diloweralkylaminohydroxyloweralkyl, acyl, aminoacyl, diaminoacyl, hydroxyacyl, hydroxy-substituted aminoacyl, hydroxy-substituted diaminoacyl, N-loweralkylaminoacyl, N,N-diloweralkylaminoacyl, hydroxy-substituted N-loweralkylaminoacyl or hydroxy-substituted N,N-diloweralkylaminoacyl; $R_4$ is hydrogen or methyl; and the pharmaceutically acceptable salts thereof.

35 Claims, No Drawings

1-EPI-FORTIMICIN A AND DERIVATIVES

BACKGROUND OF THE INVENTION

It is known that the antibacterial and pharmacological properties of many naturally produced aminoglycoside antibiotics can be altered by structural modifications. For example, certain chemical modifications in the gentamicin and kanamycin family of aminoglycoside antibiotics provide structures which are less toxic than the parent antibiotic. Further, in the same family series mentioned above, certain modifications alter the antibacterial spectrum advantageously either by increasing the intrinsic activity or increasing activity against resistant strains.

Further, historically, once an aminoglycoside antibiotic has been in clinical use for a period of time, resistant microorganisms develop. In many cases, the resistance is R-factor mediated and is attributed to the ability of the bacteria to enzymatically modify the amino or hydroxyl groups of the aminoglycoside antibiotics. Thus there is also a need for new entities which can be held in reserve to combat strains which have become resistant to treatment by the clinically used antibiotics.

The fortimicins are a relatively new class of aminoglycoside antibiotics. Fortimicin A is disclosed in U.S. Pat. No. 3,976,768 and fortimicin B in U.S. Pat. No. 3,931,400. Chemical modification of the parent fortimicins have been found to either increase the intrinsic activity of fortimicin A and B, reduce the toxicity or provide therapeutic agents which while having about the same activity, or perhaps somewhat weaker activity but are nevertheless useful as reserve antibiotics in the event resistant strains develop after a period of clinical use of one or more of the fortimicins. The 4-N-acyl derivatives of fortimicin B are disclosed in U.S. Pat. No. 4,091,032 as are the 4-N-alkylfortimicin B derivatives. The 3-O-demethylfortimicin A, fortimicin B and derivatives are disclosed in U.S. Pat. No. 4,124,756. A complete list of the fortimicin patents and pending applications is recited in the accompanying prior art statement filed herewith.

While a number of fortimicin derivatives have been made to date, and valuable therapeutic agents have been identified, the search continues for new fortimicin antibiotics which either have a broader spectrum, less ototoxicity, exhibit oral activity, etc. as well as for agents which can be held in reserve and used to treat infections caused by organisms which become resistant to fortimicin therapy. The present invention provides one such class of compounds, the 1-epi-derivatives of fortimicin A, fortimicin B and fortimicin A and B derivatives.

Summary of the Invention

The present invention relates to novel fortimicin derivatives and specifically provides 1-epi-derivatives of fortimicin A, fortimicin B, 4-N-acylfortimicin B derivatives, 4-N-alkylfortimicin B derivatives and of the corresponding 2-deoxy, 5-deoxy, 2,5-dideoxy, 3-O-demethyl, as well as the corresponding 6'-N-alkyl derivatives. The fortmicin antibiotics of this invention are useful as broad spectrum antibiotics in treating infections caused by susceptible strains of *Staphylococcus aureus, Enterobacter aerogenes, Escherichia coli, Klebsiella pneumoniae, Providencia stuartii, Pseudomonas aeruginosa, Salmonella typhimurium, Serratia marescens, Shigella sonnei, Proteus rettgeri, Proteus vulgaris* and *Proteus mirabilis.*

Intermediates useful in making the novel antibiotics are also provided as well as pharmaceutical compositions and methods.

DETAILED DESCRIPTION OF PREFERRED EMBODIMENTS

The 1-epi-fortimcin derivatives of this invention are represented by Formula I:

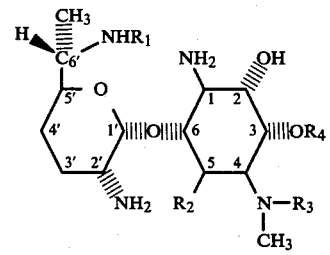

wherein: $R_1$ is hydrogen or loweralkyl; $R_2$ is hydrogen or hydroxyl, $R_3$ is selected from the group consisting of hydrogen, loweralkyl, aminoloweralkyl, diaminoloweralkyl, N-loweralkylaminoloweralkyl, N,N-diloweralkylaminoloweralkyl, hydroxyloweralkyl, aminohydroxyloweralkyl, N-loweralkylaminohydroxyloweralkyl, N,N-diloweralkylaminohydroxyloweralkyl, acyl, aminoacyl, diaminoacyl, hydroxyacyl, hydroxy-substituted amino acyl, hydroxy-substituted diaminoacyl, N-loweralkylaminoacyl, N,N-diloweralkylaminoacyl, hydroxy-substituted N-loweralkylaminoacyl or hydroxy-substituted N,N-diloweralkylaminoacyl; $R_4$ is hydrogen or methyl; and the pharmaceutically acceptable salts thereof.

The term "loweralkyl", as used herein, refers to straight or branched chain alkyl radicals having from 1 to 7 carbon atoms, including, but not limited to methyl, ethyl, n-propyl, iso-propyl, n-butyl, sec-butyl, tert-butyl, n-pentyl, 2-methylbutyl, 2,2-dimethylpropyl, n-hexyl, 2,2-dimethylbutyl, 1-methylpentyl, 2-methylpentyl, n-heptyl and the like.

The term "acyl" as used in the definition of $R_3$ in the specification and claims, refers to acyl groups represented by the formula

wherein $R_3$ is loweralkyl, i.e., acetyl, propionyl, butyryl, valeryl and the like.

The terms "aminoacyl" et seq. for $R_3$ include the naturally occurring amino acids such as glycyl, valyl, alanyl, sarcosyl, leucyl, isoleucyl, prolyl, seryl, and the like as well as groups such as 2-hydroxy-4-aminobutyryl. The amino acids residues included in the above terms can be in the L- or D- configurations or a mixture thereof, with the exception of course of glycyl.

The term "pharmaceutically acceptable salts", as used herein, refers to the non-toxic acid addition salts of the compounds of this invention which can be prepared in situ during the final isolation and purification or by separately reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and the like. It will be apparent to those skilled in the art that, depending upon the number of available amino groups for salt formation, the salts of this invention can be per-N-salts.

The compounds of Formula I, are useful as broad spectrum antibiotics when administered parenterally to a patient suffering from an infection caused by a susceptible strain of bacilli in dosages of from 10 to 100 mg/kg of body weight daily, based on lean body weight as is good medical practice with the aminoglycoside antibiotics, and preferably from about 15 to about 30 mg/kg of body weight daily. The compounds are preferably administered in divided doses, i.e. three to four times daily and can be administered by intravenous, intramuscular, intraperitoneal, or subcutaneous routes of administration for systemic activity and orally to sterilize the intestinal tract. The antibiotics of this invention can also be administered in suppository form.

The antibiotics of Formula I can be used as described above in the treatment of infections caused by susceptible strains of organisms such as *Staphylococcus aureus, Enterobacter aerogenes, Escherichia coli, Klebsiella pneumoniae, Providencia stuartii, Pseudomonas aeruginosa, Salmonella typhimurium, Shigella sonnei, Proteus rettgeri Proteus vulgaris* and *Proteus mirabilis.*

The term "susceptible strains" refers to strains of bacilli which have been demonstrated to be sensitive to a particular antibiotic in a standard in vitro sensitivity test and thus in vitro activity has been established for a particular antibiotic against a specific strain of a specific organism.

The compounds of Formula I can also be incorporated into scrub solutions for sterilizing surfaces such as laboratory benchtops, operating room surfaces and the like.

Intermediates useful in the preparation of the compounds of Formula I are also provided by the present invention and are represented by Formulae II and III:

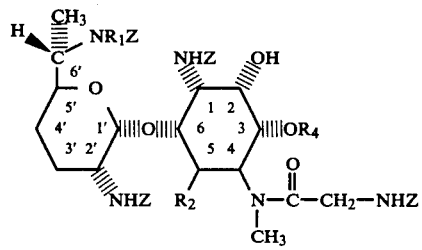

II wherein $R_1$ is hydrogen, $R_2$ is hydrogen or hydroxyl, Z is benzyloxycarbonyl and $R_4$ is methyl or hydrogen.

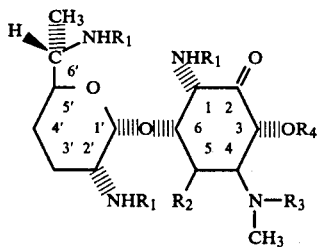

III wherein: $R_1$ is hydrogen or monocyclicaryloxycarbonyl; $R_2$ is hydrogen or hydroxy; $R_3$ is as defined in Formula I or $-COCH_2NHR_5$ wherein $R_5$ is monocyclicaryloxycarbonyl and $R_4$ is hydrogen or methyl.

Representative compounds of this invention include, but are not limited to: 1-epi-fortimicin A, 1-epi-fortimicin B, 1-epi-4-N-sarcosylfortimicin B, 1-epi-4-N-methylfortimicin B, 1-epi-4-N-ethylfortimicin B, 1-epi-4-N-n-propylfortimicin B, 1-epi-4-N-iso-propylfortimicin B, 1-epi-4-N-n-butylfortimicin B, 1-epi-4-N-sec-butylfortimicin B, 1-epi-4-N-tert-butylfortimicin B, 1-epi-4-N-n-pentylfortimicin B, 1-epi-4-N-(1-methylbutyl)fortimicin B, 1-epi-n-hexylfortimicin B, 1-epi-n-heptylfortimicin B, 1-epi-beta-aminoethylfortimicin B, 1-epi-(2-hydroxy-4-aminobutyryl)-fortimicin B, 1-epi-4-N-beta-alanylfortimicin B, 1-epi-4-N-iso-leucylfortimicin B, 1-epi-4-N-sarcosylfortimicin B, 1-epi-4-N-valylfortimicin B, 1-epi-4-N-leucylfortimicin B, 1-epi-4-N-prolylfortimicin B, 1-epi-4-N-aspartylfortimicin B, 1-epi-4-N-hydroxymethylfortimicin B, 1-epi-4-N-acetylfortimicin B, 1-epi-4-N-propionylfortimicin B, 1-epi-4-N-valerylfortimicin B, 1-epi-4-N-butyrylfortimicin B, 1-epi-5-deoxy-4-N-acetyl-fortimicin B, 1-epi-5-deoxy-4-N-propionylfortimicin B, 1-epi-5-deoxy-4-N-(2-hydroxy-4-aminobutyl)fortimicin B, 1-epi-5-deoxy-4-N-methylfortimicin B, 1-epi-5-deoxy-4-N-hydroxymethylfortimicin B, 1-epi-5-deoxy-4-N-beta-alanylfortimicin B, 1-epi-2-deoxyfortimicin B, 1-epi-5-deoxyfortimicin B, 6'-N-ethyl-1-epi-5-deoxyfortimicin A, 1-epi-5-deoxy-4-N-ethylfortimicin B, 1-epi-2-deoxy-4-N-hydroxyethylfortimicin B, 1-epi-5-deoxy-4-N-beta-aminoethylfortimicin B, 1-epi-deoxy-4-N-n-butylfortimicin B, 1-epi-5-deoxy-4-N-leucylfortimicin B, 1-epi-4-N-methyl-5-deoxyfortimicin B, 1-epi-4-N-ethyl-5-deoxyfortimicin B, 1-epi-4-N-n-propyl-5-deoxyfortimicin B, 1-epi-4-N-n-butyl-5-deoxyfortimicin B, 1-epi-4-N-n-heptyl-5-deoxyfortimicin B, 1-epi-4-N-methylamino-5-deoxyfortimicin B, 1-epi-4-N-diethylamino-5-deoxyfortimicin B, 1-epi-4-N-beta-alanyl-5-deoxy-fortimicin B, 1-epi-4-n-propylfortimicin B, 1-epi-4-N-sarcosyl-5-deoxyfortimicin B, 1-epi-4-N-acetyl-5-deoxyfortimicin B, 1-epi-4-N-butyryl-5-deoxyfortimicin B, 1-epi-4-N-(2-aminobutyryl)-5-deoxyfortimicin B, 1-epi-3-O-demethylfortimicin A, 1-epi-2-deoxy-3-O-demethylfortimicin A, 1-epi-5-deoxy-3-O-demethylfortimicin B, 1-epi-3-O-demethyl-4-N-methylfortimicin B, 1-epi-3-O-demethyl-4-N-n-heptylfortimicin B, 1-epi-3-O-demethyl-4-N-acetylfortimicin B, 1-epi-3-O-demethyl-4-N-valerylfortimicin B, 1-epi-3-O-demethyl-N-valylfortimicin B, 6'-N-methyl-1-epi-fortimicin A, 6'-N-methyl-1-epi-fortimicin B and the like and the corresponding salts such as 1-epi-fortimicin A tetrahydrochloride and the like.

Generally speaking, 1-epi-fortimicin A can be conveniently prepared by the methods set forth in Examples 1—3.

1-Epi-fortimicin B derivatives can be prepared by removing the $C_4N$-glycyl moiety from 1-epi-fortimicin A by basic or acidic hydrolysis, using, for example, 0.2 N methanolic sodium hydroxide to obtain 1-epi-fortimicin B. 1-Epi-fortimicin B can then be selectively protected at the three primary amino groups by treatment with, for example, the N-hydroxysuccinimide ester of benzyloxycarbonate or a similar active ester such as those described in U.S. Pat. No. 4,091,032 which discloses the 4-N-acyl derivatives of fortimicin B and their method of preparation which is generally followed in the preparation of the corresponding 1-epi-derivatives of this invention.

The per-N-protected intermediate can then be reacted with a carboxylic acid derivative such as a carboxylic acid ester or a carboxylic acid azide, following the methodology set forth in U.S. Pat. No. 4,091,032 and that commonly used in peptide synthesis to obtain the desired 4-N-acyl (using the term broadly to include aminoacyl, hydroxyacyl, etc.) intermediates. The above-referred to active carboxylic acid esters can be prepared by reacting the appropriate carboxylic acid, $R_3COOH$ with, for example 1-hydroxybenzotriazole-N-hydroxysuccinimide, N-hydroxy-5-norbornene-2,3-dicarboximide, etc. according to the method of Fugino et al. *Chem Phar. Bull. Japan* 22, 1857 (1974).

The 4-N-alkyl derivatives of this invention are obtained by reduction of the $C_4$-amides to the corresponding 4-N-alkyl compounds by treatment with diborane as taught in examples 7 and 8.

6'-N-methylation can be conveniently effected by subjecting the 1-epi-fortimicin to be 6'-N-methylated to selective N-carbobenzyloxylation with one mole of an active ester of benzylcarbonate, and reducing the 6'-N-carbobenzoxy derivative with a suitable metal hydride such as lithium aluminum hydride as taught by Umezawa et al. U.S. Pat. No. 3,925,353 and in commonly assigned co-pending United States Patent application Ser. No. 863,108 which discloses the 6'-N-alkyl derivatives of fortimicin A and B and the 4-N-acyl and alkyl fortimicin B derivatives.

Other alkyl groups can be attached at the 6'-N-position by treating the 1-epi-fortimicin to be 6'-N-alkylated with one mole of the appropriate aldehyde and reducing the resulting Schiff base with hydrogen in the presence of a precious metal catalyst such as platinum oxide or with a suitable metal hydride such as sodium cyanoborohydride.

O-demethylation of the 1-epi-fortimcins of the present invention can be accomplished by treating the compounds to be 3-O-demethylated with boron trihalide neat or in the presence of an inert solvent such as a hydrocarbon solvent or a halogenated hydrocarbon solvent like methylene chloride.

5-Deoxygenation can be accomplished by treating 1-epi-tetra-N-benzyloxycarbonylfortimicin A with N,N-thiocarbonyldiimidazole in triethylamine, followed by treatment of the resulting 5-O-thiocarbonylimidazolide intermediate with tri-n-butylstannane in dioxane to provide 1-epi-5-deoxytetra-N-benzyloxcarbonylfortimicin A. Treatment of the latter with methanolic hydrogen chloride in the presence of palladium on carbon results in 1-epi-5-deoxyfortimicin A tetrahydrochloride which can then be further modified if desired to provide the 1-epi-5-deoxyfortmicin B derivatives of this invention.

The following examples further illustrate the present invention.

EXAMPLE 1

1-Epi-2-deoxy-2-oxo-tetra-N-benzyloxycarbonylfortimicin A

A solution of tetra-N-benzyloxycarbonylfortimicin A (5.0 g, 5.3 millimole) in acetone (100 ml) is treated at 4° C. with Jones Reagent (aqueous chromic acid in acetone, 4.0 ml). The mixture is maintained at 4° C. for 35 minutes and poured into water (7 volumes). The products are extracted with methylene chloride and the solution dried over magnesium sulfate. Solvent is removed and the residue is chromatographed over a column of silica gel to give 1-epi-2-deoxy-2-oxo-tetra-N-benzyloxycarbonylfortimicin A (1.81 g).

Analysis calcd. for $C_{49}H_{57}N_5O_{14}$: C, 62.61; H, 6.11; N, 7.45. Found: C, 62.74; H, 6.03; N, 7.43.

EXAMPLE 2

1-Epi-tetra-N-benzyloxycarbonylfortimicin A

A solution of the above prepared 1-epi-2-deoxy-2-oxo-tetra-N-benzyloxycarbonylfortimicin A (330 mg, 0.34 millimole) in isopropyl alcohol (9 ml) is treated with a saturated solution of sodium borohydride in isopropyl alcohol (1 ml). The mixture is allowed to stand at room temperature for forty-five minutes. The excess borohydride is consumed by the addition of acetone and solvent is removed. Chromatography of the residue over a column of silica gel yields 191 mg of the desired product, 1-epi-tetra-N-benzyloxycarbonylfortimicin A.

EXAMPLE 3

1-Epi-fortimicin A tetrahydrochloride

A solution of 1-epi-tetra-N-benzyloxycarbonyl-fortimicin A (259 mg., 0.27 millimole) in methanolic hydrochloric acid (22 ml, 0.2 N) is hydrogenated over 5% Pd/C at three atmospheres for four hours. Catalyst is removed by filtration and the filtrate is evaporated to give 1-epi-fortimicin A tetrahydrochloride (163 mg. PMR spectrum measured in $D_2O$ at pD 5.21 from external TMS characteristic peaks at $\delta$ 1.80(3 H) doublet (J=7.0 Hz) (C-$CH_3$); $\delta$ 3.55(3 H) singlet (N$CH_3$); $\delta$ 3.95 (3H) singlet (O$CH_3$); $\delta$ 4.53 (2H) AB quartet (gly $CH_2$); $\delta$ 5.88 (1H) doublet (J=3.4 Hz) ($C_{1'}$-H).

EXAMPLE 4

1-Epi-2-deoxy-2-oxo-tetra-N-benzyloxycarbonylfortimcin A (Alternate Method)

A solution of tetra-N-benzyloxycarbonylfortimicin A (1.2 g, 1.3 millimoles) in dimethylsulfoxide (4.0 ml) and acetic anhydride (2.8 ml) is allowed to stand at room temperature for 24 hours. The solution is diluted with water (100 ml) and the crude product is extracted with chloroform. The extract is dried over magnesium sulfate, filtered and solvent removed from the filtrate. The residue is chromatographed on a column of silica gel in ethyl acetate-hexane [7:3(v/v)] to afford 350 mg of the desired product.

EXAMPLE 5

1-Epi-tetra-N-benzyloxycarbonylfortimicin A

Sodium cyanoborohydride (14.4 g) is added in small portions to a solution of 1-epi-2-deoxy-2-oxo-tetra-N-benzyloxycarbonylfortimicin A (20 g, 21.3 millimoles) in methanol (200 ml). The pH of the reaction is maintained at about 3 during the reaction by the addition of appropriate quantitites of 2-N-methanolic hydrogen chloride. The reaction is diluted with water (2.5 l) and the crude product is extracted with chloroform. Solvent is removed from the reaction by filtration and the crude product dried over magnesium sulfate, filtered, extracted and the residue chromatographed over a column of silica gel in an ethyl acetate-hexane mixture [7.3 (v/v)] to give 15.3 g of 1-epi-tetra-N-benzyloxycarbonylfortimicin A.

EXAMPLE 6

1-Epi-4-N-beta-aminoethyl-tetra-N-benzyloxycarbonylfortimicin B

1-Epi-tetra-N-benzyloxycarbonylfortimicin A (1.0 g, 1.06 mmoles) is dissolved in dioxane (20 ml), stirred under an atmosphere of nitrogen and treated with a solution of 1 M diborane in tetrahydrofuran (5.0 ml). Excess diborane is destroyed by careful addition of methanol after nine hours and the mixture is evaporated to dryness under reduced pressure. Chromatography of the residue over a column of silica gel eluted with ethyl acetate-hexane mixture afforded 571 mg of product. PMR spectrum in $CDCl_3$ with TMS as internal reference $\delta$ 1,04 (3H) doublet (J=6.0 Hz) ($CCH_3$); $\delta$ 2.43 (3H) singlet ($NCH_3$); $\delta$ 3.31 (3H) singlet ($OCH_3$).

EXAMPLE 7

1-Epi-4-N-beta-aminoethylfortimicin B hydrochloride

1-Epi-4-N-beta-aminoethyl-tetra-N-benzyloxycarbonylfortimicin B (348 mg) is hydrogenated in methanolic hydrogen chloride (37.5 ml, 0.2 N) over 5% Pd/C (0.35 g) at three atmospheres for six hours. The catalyst is removed by filtration and the filtrate concentrated to yield the hydrochloride salt of 1-epi-4-N-beta-aminoethylfortimicin B.

EXAMPLE 8

1-Epi-tetra-N-benzyloxycarbonylfortimicin A-5-O-thiocarbonylimidazolide

1-Epi-tetra-N-benzyloxycarbonylfortimicin A (2.0 g) N,N-thiocarbonyldiimidazole (1.0 g) and triethylamine (1 ml) in 40 ml of 1,2-dichloroethane are heated under reflux for 2.5 hours. Solvent is removed under reduced pressure and the residue is chromatographed on a column of silica gel eluted with 1,2-dichloroethane-ethanol [96:4(v/v)]. Later fractions are combined and concentrated to yield 710 mg of desired product. PMR spectrum in $CD_3COCD_3$ with TMS as internal reference $\delta$ 1,08 (3H) doublet (J=7.0 Hz) ($CCH_3$); $\delta$ 2.99 (3H) singlet ($NCH_3$); $\delta$ 3.46 (3H) singlet ($OCH_3$).

EXAMPLE 9

1-Epi-5-deoxy-tetra-N-benzyloxycarbonylfortimicin A

A solution of 1-epi-tetra-N-benzyloxycarbonylfortimicin A-5-O-thiocarbonylimidazolide (700 mg) in dioxane (20 ml) is added slowly to a solution of tri-N-butylstannane in dioxane (20 ml) and heated under reflux in an atmosphere of nitrogen. After three hours, the mixture is cooled and solvent is removed under reduced pressure. The residue is chromatographed on a column of silica gel eluted with ethyl acetate. Later fractions are combined and concentrated to give 450 mg of product.

EXAMPLE 10

1-Epi-5-deoxyfortimicin A tetrahydrochloride

1-Epi-5-deoxy-tetra-N-benzyloxycarbonylfortimicin A (290 mg) in methanolic hydrogen chloride (25 ml, 0.2 N) is shaken with hydrogen in the presence of 5% Pd/C (300 mg) for four hours. The mixture is filtered and the filtrate is concentrated to yield 164 mg of 1-epi-5-deoxyfortimicin A tetrahydrochloride. The carbon magnetic resonance spectrum is set forth in the Table 1 as are the spectra of the products of the preceding examples. PMR spectrum in $D_2O$ with TMS as external reference $\delta$ 1.82 (3H) doublet (J=6.8 Hz) ($CCH_3$); $\delta$ 3.42 (3H) singlet ($NCH_3$); $\delta$ 3.92 (3H) singlet ($OCH_3$); $\delta$ 4.55 (2H) singlet (gly-$CH_2$); $\delta$ 5.91 (1H) doublet (J=3.5 Hz) $C_{1'}$-H).

EXAMPLE 11

1-Epi-2-deoxy-2-oxofortimicin A tetrahydrochloride

1-Epi-2-deoxy-2-oxo-tetra-N-benzyloxycarbonylfortimicin A (260 mg) in methanolic hydrogen chloride (22 ml, 0.2 N) is hydrogenated over 5% Pd/C at three atmospheres for four hours. Catalyst is removed by filtration and the filtrate evaporated to yield 150 mg of the desired product. PMR spectrum in $D_2O$ with TMS as external reference $\delta$ 1.85 (3H) doublet (J=7.0 Hz) ($CCH_3$); $\delta$ 3.65 (3H) singlet ($NCH_3$); $\delta$ 4.07 (3H) singlet ($OCH_3$); $\delta$ 4.62 (2H) AB quartet (gly-$CH_2$); $\delta$ 5.99 (1H) doublet (J=3.5 Hz) ($C_{1'}$-H).

EXAMPLE 12

1-Epi-3-O-demethyl-tetra-N-benzyloxycarbonylfortimicin A

1-Epi-fortimicin A free base (1.17 g) is suspended in anhydrous dichloromethane (35 ml), treated with boron tribromide (13.8 ml) and allowed to stand for four days at room temperature. The reaction mixture is evaporated to dryness under reduced pressure and the residual boron removed as methyl boronate by repeated addition of methyl alcohol followed by removal of the solvent under reduced pressure. The crude product is treated with the benzyloxycarbonyl ester of N-hydroxysuccinimide (3.0 g) in a mixture of water (4 ml) and acetonitrile (20 ml) and triethylamine (1.0 ml) at room temperature overnight. Solvent is removed under reduced pressure and the residue chromatographed over a column of silica gel eluted with ethyl acetate-hexane[7:3 (v/v)] to yield 1-epi-3-O-demethyl-tetra-N-benzyloxycarbonylfortimicin A (295 mg).

EXAMPLE 13

1-Epi-3-O-demethylfortimicin A tetrahydrochloride

1-Epi-3-O-demethyl-tetra-N-benzyloxycarbonylfortimicin A (295 mg) in 0.2 N-methanolic hydrogen chloride (25 ml) is shaken in the presence of palladium on charcoal (0.3 g, 5%) under three atmospheres of hydrogen for four hours. The mixture is filtered and the filtrate is concentrated under vacuum with several additions and removals of methanol to yield 1-epi-3-O-demethylfortimicin A tetrahydrochloride (165 mg).

The carbon magnetic resonance spectra of the compounds of examples 1—3, 6—11 and 13 are set forth in Table I. Spectra were recorded in deuterochloroform (Examples 1, 2, 6 and 9; deuterium oxide (Examples 3, 10, 11 and 13) and perdeuteroacetone (Example 8). Only signals assigned to the carbons of the fortimicin A skeleton are shown and these are described in ppm downfield from tetramethylsilane. Assignments are made from analogy with other known fortimicin derivatives and with known effects of structural changes on carbon magnetic resonance spectra. Interchanges of assignments of resonances of similar chemical shifts can be made without affecting the characterization of the compounds or the sturctural inferences of the spectra.

TABLE I

CARBON MAGNETIC RESONANCE SPECTRA

| | Ex 1 | Ex 2 | Ex 3 | Ex 6 | Ex 7 | Ex 8 | Ex 9 | Ex 10 | Ex 11 | Ex 13 |
|---|---|---|---|---|---|---|---|---|---|---|
| $C_1$ | 57.9 | 50.2 | 51.4 | 49.7 | 49.2 | 50.7 | 49.5 | 51.6 | 56.9 | 51.8 |
| $C_2$ | 201.0 | 66.2 | 69.5 | 68.7 | 28.5 | 68.2 | 69.3 | 70.7 | 201.7 | 70.9 |
| $C_3$ | 79.4 | 71.4 | 75.2 | 75.8 | 69.4 | 75.5 | 79.4 | 79.1 | 79.7 | 64.7 |
| $C_4$ | 58.5 | 50.6 | 51.4 | 55.7 | 67.6 | 51.3 | 53.3 | 52.6 | 60.0 | 52.0 |
| $C_5$ | 70.7 | 68.2 | 70.2 | 68.7 | 68.1 | 82.5 | 27.1 | 28.4 | 67.0 | 67.8 |
| $C_6$ | 81.9 | 74.1 | 79.1 | 76.5 | 73.8 | 76.1 | 74.8 | 75.6 | 74.9 | 74.0 |
| $C_1'$ | 100.1 | 99.7 | 97.8 | 96.2 | 95.9 | 100.2 | 96.4 | 95.6 | 92.7 | 92.5 |
| $C_2'$ | 50.2 | 49.6 | 49.9 | 49.7 | 51.7 | 50.4 | 50.8 | 49.9 | 51.7 | 49.4 |
| $C_3'$ | 23.3 | 23.8 | 25.5 | 24.0 | 21.7 | 24.7 | 24.9 | 25.5 | 21.0 | 21.3 |
| $C_4'$ | 26.8 | 26.8 | 27.2 | 27.1 | 26.3 | 27.5 | 27.5 | 27.2 | 26.1 | 26.3 |
| $C_5'$ | 71.5 | 71.4 | 72.2 | 71.4 | 71.0 | 71.7 | 71.8 | 71.7 | 71.2 | 70.4 |
| $C_6'$ | 49.6 | 48.7 | 48.6 | 48.7 | 50.0 | 50.1 | 50.6 | 47.9 | 49.4 | 49.3 |
| $C_7'$ | 18.2 | 18.0 | 16.6 | 18.2 | 15.1 | 17.6 | 18.1 | 16.2 | 15.2 | 15.2 |
| $OCH_3$ | 58.0 | 56.3 | 56.1 | 58.0 | 56.7 | 55.9 | 56.6 | 56.2 | 56.5 | — |
| $NCH_3$ | 32.1 | 32.9 | 31.9 | 38.9 | 40.3 | 32.1 | 32.1 | 29.1 | 31.6 | 31.8 |
| Gly | 43.2 | 43.1 | 42.9 | 40.0 | 53.5 | 43.6 | 43.5 | 43.0 | 41.3 | 41.3 |
| | 167.7 | 169.9 | — | 53.6 | 35.4 | 170.8 | 170.2 | — | 169.0 | 169.1 |

The in vitro antibiotic activity is determined by a two-fold dilution test using Mueller-Hinton agar, 10 ml per Petri plate. The inoculum of approximately $1 \times 10^5$ of the indicated test organism is delivered by the Steer's replicator. The test is incubated at 37° C. for 24 hours.

The in vitro antibiotic spectra for representative compounds of this invention, 1-epi-fortimicin A, and 3-O-demethyl-1-epi-fortimicin A are set forth in Table II.

TABLE II

MINIMUM INHIBITORY CONCENTRATION (mcg/ml) OF 1-EPI FORTIMICINS

| Organism | Ex. 3 MIC(mcg/ml) | Ex. 13 MIC(mcg/ml) |
|---|---|---|
| Staphylococcus aureus Smith | 1.56 | 0.78 |
| Streptococcus faecalis 10541 | 100 | 50 |
| Enterobacter aerogenes 13048 | 6.2 | 3.1 |
| Escherichia coli JUHL | 12.5 | 6.2 |
| Escherichia coli BL 3676(RES) | 50.0 | 25 |
| Escherichia coli 76-2 | 6.2 | 3.1 |
| Klebsiella pneumoniae 10031 | 3.1 | 3.1 |
| Klebsiella pneumoniae KY 4262 | 6.2 | 6.2 |
| Providencia stuartii 1577 | 3.1 | 6.2 |
| Pseudomonas aeruginosa BMH #10 | 0.78 | 0.78 |
| Pseudomonas aeruginosa KY 8512 | 25 | 6.2 |
| Pseudomonas aeruginosa KY 8516 | 100 | 25 |
| Pseudomonas aeruginosa 209 | 100 | 100 |
| Pseudomonas aeruginosa 27853 | 50 | 6.2 |
| Salmonella typhurium Ed. #9 | 3.1 | 3.1 |
| Serratia marcescens 4003 | 3.1 | 3.1 |
| Shigella sonnei 9290 | 12.5 | 12.5 |
| Proteus rettgeri U-6333 | 3.1 | 3.1 |
| Proteus vulgaris JJ | 12.5 | 3.1 |
| Proteus mirabilis Fin #9 | 12.5 | 6.2 |

The compounds of this invention are active as systemic antibiotics when administered by parenteral routes of administration, i.e., by the intramuscular, intravenous, intraperitoneal or subcutaneous routes of administration. The compounds can also be administered orally in those instances where it is desirable to sterilize the intestinal tract and can additionally be applied topically or administered in suppository form.

Preparations according to this invention for parenteral administration include sterile aqueous or non-aqueous solutions, suspensions, or emulsions. Examples of non-aqueous solvents or vehicles are propylene glycol, polyethylene glycol, vegetable oils such as olive oil, and injectable organic esters such as ethyl oleate. Such dosage forms can also include adjuvants such as preserving, wetting, emulsifying and dispersing agents. They may be sterilized by, for example, filtration through a bateria-retaining filter, by incorporating sterilizing agents into the compositions, etc. They can also be manufactured in the form of sterile solid compositions which can be dissolved in sterile water, or some other sterile injectable medium immediately before use.

Compositions for rectal administration are preferably suppositories which may contain, in addition to the active substance, excipients such as cocoa butter or a suppository wax.

Solid dosage forms for oral administration include capsules, tablets, pills, powders and granules. In such solid dosage forms, the active compound is admixed with at least one inert diluent such as sucrose, lactose or starch, unless filled capsules are employed, in which case, no other ingredient is necessary. Such dosage forms can also comprise, as is normal practice, additional substances other than inert diluents, for example, lubricating agents such as magnesium stearate. Buffering agents can also be included and, in the case of tablets and pills, enteric coatings may be employed to ensure they reach the intestinal tract.

The dosage of the active ingredient in the compositions of this invention may be varied so long as an antibacterially effective amount of active ingredient is present. The selected dosage depends upon the desired therapeutic effect, on the route of administration and on the duration of treatment. The dosage forms are prepared so that the administration of from 10 to 100 and preferably 15 to 30 mg/kg of body weight of antibiotic daily, based on lean body weight in the case of overweight patients, is accomplished.

Several 1-epi-2-deoxyfortimicins have been reported to have been produced by the fermentation of a suitable Saccharapolyspora species, the 1-epi-2-deoxyfortimicin A ($R_3$=COCH$_2$NH$_2$) and the corresponding compounds where $R_3$ is —COCH$_2$NHCONH$_2$ and —COCH$_2$NHCHO. See Derwent DT 2813-021, Week A 11, p. B3(1978).

We claim:

1. A 1-Epi fortimicin represented by the formula

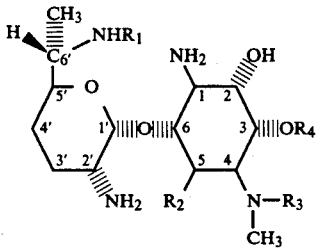

wherein: $R_1$ is hydrogen or loweralkyl; $R_2$ is hydrogen or hydroxyl, $R_3$ is selected from the group consisting of hydrogen, loweralkyl, aminoloweralkyl, diaminoloweralkyl, N-loweralkylminoloweralkyl, N,N-diloweralkylaminoloweralkyl, hydroxyloweralkyl, aminohydroxyloweralkyl, N-loweralkylaminohydroxyloweralkyl, N,N-diloweralkylaminohydroxyloweralkyl, acyl, aminoacyl, diaminoacyl, hydroxyacyl, hydroxy-substituted aminoacyl, hydroxy-substituted diaminoacyl, N-loweralkylaminoacyl, N,N-diloweralkylaminoacyl, hydroxy-substituted N-loweralkylaminoacyl and hydroxy-substituted N,N-diloweralkylaminoacyl; $R_4$ is hydrogen or methyl; and the pharmaceutically acceptable salts thereof.

2. A compound of claim 1 wherein $R_2$ is hydroxy.
3. A compound of claim 1 wherein $R_2$ is hydroxy and $R_1$ is hydrogen.
4. A compound of claim 1 wherein $R_2$ is hydroxy, $R_1$ is hydrogen and $R_4$ is methyl.
5. A compound of claim 1 wherein $R_2$ is hydroxy, $R_1$ is hydrogen and $R_4$ is hydrogen.
6. A compound of claim 1 wherein $R_4$ is hydrogen.
7. A compound of claim 1 wherein $R_1$ is loweralkyl.
8. A compound of claim 1 wherein $R_2$ is hydrogen.
9. A compound of claim 1 wherein $R_2$ is hydrogen and $R_4$ is hydrogen.
10. 1-Epi-fortimicin A or a pharmaceutically acceptable salt thereof.
11. A compound of claim 1: 1-epi-fortimcin B or a pharmaceutically acceptable salt thereof.
12. A compound of claim 1: 1-epi-4-N-beta-aminoethylfortimicin B or a pharmaceutically acceptable salt thereof.
13. A compound of claim 1: 1-epi-5-deoxyfortimicin A or a pharmaceutically acceptable salt thereof.
14. A compound of claim 1: 1-epi-5-deoxyfortimicin B or a pharmaceutically acceptable salt thereof.
15. A compound of claim 1: 1-epi-3-O-demethylfortimicin A or a pharmaceutically acceptable salt thereof.
16. A compound of claim 1: 1-epi-3-O-demethylfortimicin B or a pharmaceutically acceptable salt thereof.
17. A compound of claim 1: 1-epi-4-N-methylfortimicin A or a pharmaceutically acceptable salt thereof.
18. A compound of claim 1: 1-epi-4-N-methylfortimicin B or a pharmaceutically acceptable salt thereof.
19. A compound of claim 1: 6'-N-methyl-1-epi-fortimicin A or a pharmaceutically acceptable salt thereof.
20. A compound of claim 1: 6'-N-methyl-1-epi-fortimicin B or a pharmaceutically acceptable salt thereof.
21. A compound of claim 1: 1-epi-4-N-(2-hydroxy-beta-aminoethyl)fortimicin B or a pharmaceutically acceptable salt thereof.
22. A pharmaceutical composition comprising an antibacterially effective amount of a compound of claim 1 and a pharmaceutically acceptable carrier or diluent.
23. The composition of claim 22 wherein the compound is 1-epi-fortimicin A or a pharmaceutically acceptable salt thereof.
24. The composition of claim 22 wherein the compound is 1-epi-3-O-demethylfortimicin A or a pharmaceutically acceptable salt thereof.
25. The composition of claim 22 wherein said compound is 1-epi-3-O-demethylfortimicin B or a pharmaceutically acceptable salt thereof.
26. The composition of claim 22 wherein said compound is 1-epi-5-deoxyfortimicin A or a pharmaceutically acceptable salt thereof.
27. The composition of claim 22 wherein said compound is 1-epi-5-deoxyfortimicin B or a pharmaceutically acceptable salt thereof.
28. A 1-epi-fortimicin intermediate represented by the formula wherein $R_1$ is hydrogen, $R_2$ is hydrogen or hydroxyl, Z is benzyloxycarbonyl, and $R_4$ is methyl or hydrogen.
29. A compound of claim 28: 1-epi-tetra-N-benzyloxycarbonylfortimicin A.
30. A compound of claim 28: 1-epi-3-O-demethyltetra-N-benzyloxycarbonylfortimicin A.
31. A compound of claim 28: 1-epi-5-deoxy-tetra-N-benzyloxycarbonylfortimicin A.
32. A 1-epi-2-deoxy-2-oxofortimicin intermediate represented by the formula wherein: $R_1$ is hydrogen or monocyclicaryloxycarbonyl; $R_2$ is hydrogen or hydroxy; $R_3$ is selected from the group consisting of hydrogen, loweralkyl, aminoloweralkyl, diaminoloweralkyl, N-loweralkylaminoloweralkyl, N,N-diloweralkylaminoloweralkyl, hydroxyloweralkyl, aminohydroxyloweralkyl, N-loweralkylaminohydroxyloweralkyl, N,N-diloweralkylaminohydroxyloweralkyl, acyl, aminoacyl, diaminoacyl, hydroxyacyl, hydroxy-substituted aminoacyl, hydroxy-substituted diaminoacyl, N-loweralkylaminoacyl, N,N-diloweralkylaminoacyl, hydroxy-substituted N-loweralkylaminoacyl, hydroxy-substituted N,N-diloweralkylaminoacyl and —COCH$_2$NHR$_5$ wherein $R_5$ is monocyclicaryloxycarbonyl; and $R_4$ is methyl or hydrogen; and, when $R_1$ is hydrogen, the pharmaceutically acceptable salts thereof.
33. A compound of claim 32: 1-epi-2-deoxy-2-oxo-tetra-N-benzyloxycarbonylfortimicin A.
34. A compound of claim 32: 1-epi-2-deoxy-2-oxofortimicin A or a pharmaceutically acceptable salt thereof.
35. A compound of claim 32: 1-epi-2-deoxy-2-epi-fortimicin B or a pharmaceutically acceptable salt thereof.

* * * * *

UNITED STATES PATENT AND TRADEMARK OFFICE
CERTIFICATE OF CORRECTION

PATENT NO. : 4,218,442
DATED : August 19, 1980
INVENTOR(S) : James B. McAlpine, et. al.

It is certified that error appears in the above—identified patent and that said Letters Patent is hereby corrected as shown below:

On the title page,
In the Abstract, at column 2, lines 11-22 and in claim 1, that portion of the formula reading 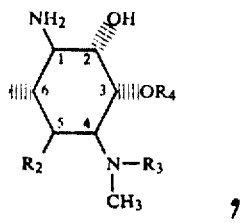 , should read

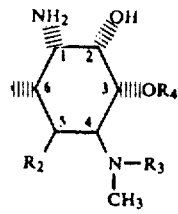

Signed and Sealed this

Eleventh Day of May 1982

[SEAL]

Attest:

GERALD J. MOSSINGHOFF

Attesting Officer    Commissioner of Patents and Trademarks